United States Patent [19]
Szapiro et al.

[11] Patent Number: 5,643,224
[45] Date of Patent: Jul. 1, 1997

[54] SAFETY VALVE PLUG FOR DISPOSABLE PRE-FILLED SYRINGES

[76] Inventors: Jaime Luis Szapiro; Leonardo Szames; Saúl Moreno, all of Tabaré 1641, Buenos Aires, Argentina

[21] Appl. No.: 379,169

[22] Filed: Jan. 27, 1995

[30] Foreign Application Priority Data

Mar. 4, 1994 [AR] Argentina ................... 327575
Aug. 19, 1994 [AR] Argentina ................... 329146

[51] Int. Cl.$^6$ ............................................. A61M 5/315
[52] U.S. Cl. ........................... 604/238; 604/236; 604/228
[58] Field of Search .............................. 604/236, 238, 604/187.218, 228, 190, 213, 215, 256, 247, 254

[56] References Cited

U.S. PATENT DOCUMENTS

| | | | |
|---|---|---|---|
| 1,179,560 | 4/1916 | Reed | 604/236 |
| 1,707,880 | 4/1929 | Sheets | 604/238 X |
| 2,893,390 | 7/1959 | Lockhart | 604/238 |
| 3,850,348 | 11/1974 | Bessot et al. | 604/236 X |
| 3,941,128 | 3/1976 | Baldwin | 604/238 |
| 4,233,975 | 11/1980 | Yerman | 604/236 X |
| 4,460,357 | 7/1984 | Cohen | 604/238 |
| 4,479,801 | 10/1984 | Cohen | 604/238 |
| 4,915,692 | 4/1990 | Vevlier | 604/110 |
| 5,352,203 | 10/1994 | Vallelunga et al. | 604/110 |

*Primary Examiner*—Robert A. Hafer
*Assistant Examiner*—V. Alexander
*Attorney, Agent, or Firm*—Bachman & LaPointe, P.C.

[57] ABSTRACT

The invention relates to a safety valve plug to be used in pre-filled syringes, of the kind comprising a cylindrical hollow body into which a coaxial plunger is displaced, projecting outwardly from one of the bases; while a conical portion is defined at the opposite base, the conical portion receiving the injection needle and being called "plugging cone", the valve plug being snug fit inside said "plugging cone" with its end head bearing on the mouth thereof, said valve plug comprising a substantially cylindrical solid body having a conical end portion and the other portion, defining its head, being cylindrical and of a cross section larger than the rest of the body; the cylindrical body having, following said conical end, two faceted faces extending adjacent the head.

6 Claims, 3 Drawing Sheets

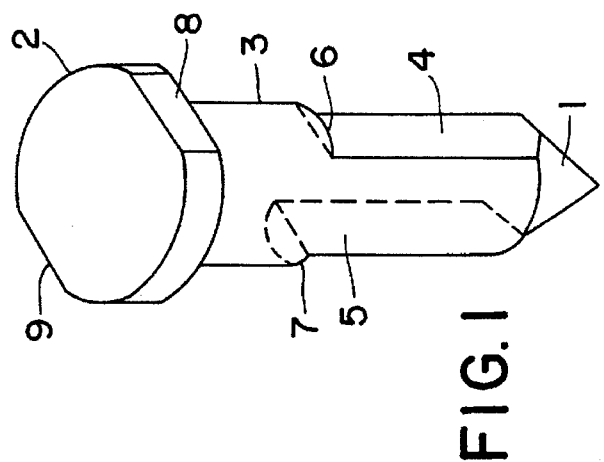
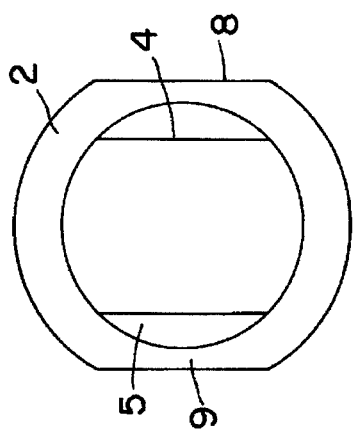
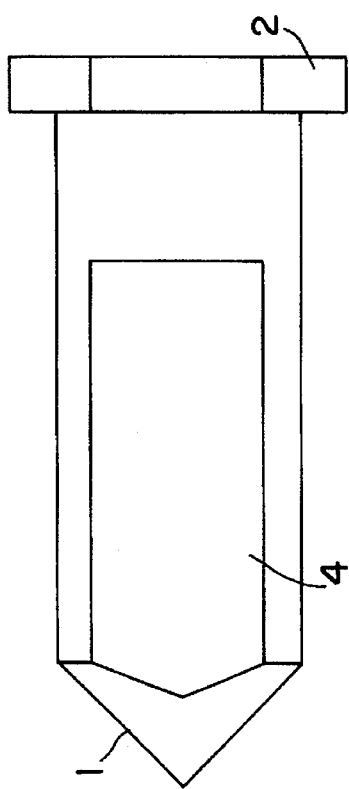
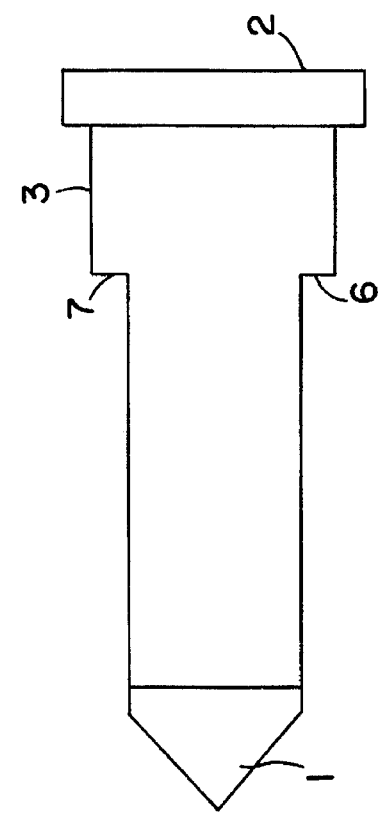

SAFETY VALVE PLUG FOR DISPOSABLE PRE-FILLED SYRINGES

FIELD OF THE INVENTION

The instant invention relates to a safety valve plug, to be used in disposable syringes, providing a tight seal to the interior of the body wherein the liquid to be injected is contained, preventing contact thereof with the needle; thus affording several operating advantages.

More particularly, the instant invention relates to a plug having a particular shape, which allows its acting as tight closure plug, automatically releasable, without being handled by the user.

Pre-filled disposable syringes on which such plugs are used are those comprised by a main cylindrical hollow body, at the interior of which a coaxial plunger displaces; said inner space comprising the transient housing chamber for the liquid to be injected. A manually operated plunger acts inside this chamber, projecting outwardly, the operating head of which acts by snug fit at the inner wall of said main body. The upper base of the main body defines a substantially conical spout, tapering outwardly, usually called "plugging cone" since it couples the needle to the syringe.

In this kind of disposable pre-filled syringes, needles are housed inside a protecting sheath which, while enclosing the needle and being coupled thereto, thus maintaining the needle tight and isolated, has means for coupling it to the syringe.

Coupling means, that of the needle with respect to the syringe main body, as well as that of its protecting sheath, assures permanent isolation of the liquid contents, before and during injection. Thus, the coupling at the rear end of the needle forms a tight closure against the inner wall of the sheath at said region.

PRIOR ART

Disposable syringes are known, as those having a basic structure like that indicated above, mainly in what concerns to means providing liquid contents isolation and isolation of the needle from the environment.

Some syringes include other internal means providing tightness at the housing and liquid circulation regions, thus isolating the different compartments between each other when the syringe is not used. These inner isolation means may be automatically deactivated by plunger shifting at the time the injection is applied.

Disadvantages of such inner isolation means are related with blockage of the normal delivery of liquid during injection and dragging of particles thereof which would be carried by the liquid during injection.

Another reference of prior art, owned by the applicants of this case, consists in the inclusion of a collapsible sheet preventing communication between two inner subsequent chambers of the same syringe and between the interior of said syringe and the interior of the needle plugging cone. Such sheets collapse, thus allowing passage of liquid, by means of the axial pressure of the plunger during injection.

In other pre-filled double chamber disposable syringes, chamber bodies are coaxial and one after the other one. These syringes are used for medicines comprising liquid and solid media which are mixed at the time of injection. The lower chamber body containing the liquid medium displaces, with minimum play, inside the upper chamber body. Between both chambers there is an elastomeric dividing septum which, being solidary to the lower chamber body, prevents internal communication between both chambers.

Known syringes should include means for imperforating said septum in order to allow passage of the liquid medium at the upper chamber. In those cases, imperforation of the septum implies, in all probability, contamination of the contents with particles of the elastomeric material to be imperforated.

These syringes have been successful in practice and have passed various tests regarding tightness of the liquid container and circulation of liquid, as well as regarding their safe use for the patient and the operator. However, in order to further improve liquid isolation, the instant invention incorporates the use of a novel safety valve plug.

SUMMARY OF THE INVENTION

The valve plug of the invention maintains liquid isolated from the needle interior until injection is carried out. Therefore, during introduction of the needle in the "plugging cone" of the syringe and withdrawal of the protecting sheath in order to carry out injection, liquid is isolated at the interior of the syringe main body, thus assuring that during coupling and uncoupling actions no undesired leakage or spoilage takes place.

To this end, the valve plug of the invention is located inside the "plugging cone" of the syringe such that its upper portion completely closes the mouth in front of the injection needle. Due to the particular shape, this plug releases liquid towards the needle only when hydraulic pressure is produced from the syringe plunger.

Disadvantages of the prior art are overcome with the valve plug of the instant invention, since pressure of the liquid medium when pushed by the syringe plunger produces displacement thereof thus opening communication between both chambers without any risk of contamination.

BRIEF DESCRIPTION OF THE DRAWINGS

A preferred, non-limiting, embodiment of the invention will be hereinbelow described in connection with the accompanying drawings, in which:

FIG. 1 is a perspective view showing the valve plug according to the instant invention.

FIG. 2 is a side view showing one of the longitudinal faceted faces of the plug of FIG. 1.

FIG. 3 is a side view, similar to that of FIG. 2, showing another longitudinal faceted face of the valve plug.

FIG. 4 is an upper plan view of the valve plug of the above drawings.

In all figures the same reference numerals designate the same or equivalent parts.

DETAILED DESCRIPTION OF THE INVENTION

Figure 5:
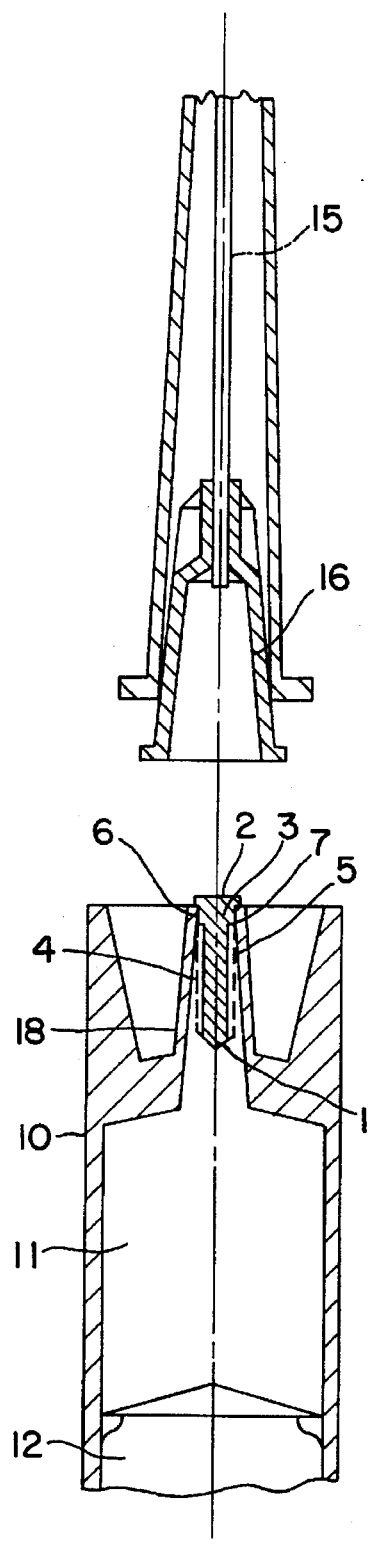
FIG. 5 is a longitudinal section showing the syringe and needle assembly, including the valve plug according to the invention.

As shown in FIGS. 1 to 4, the valve plug of the invention is a solid body of substantially cylindrical shape, having an acute and tapered lower end 1 and an upper head 2 having a larger cross section than the rest of the body, maintaining the cylindrical shape. Following the lower end 1 the plug has two equal, opposed and parallel faceted faces 4 and 5, thus determining corresponding shoulders 6 and 7 which are important for the assembly operation. Further, said cylindrical upper head 2 also has two equal, opposed and symmetrical side faceted faces 8 and 9 which, in turn, are parallel to mentioned faceted faces 4 and 5.

Figure 6:
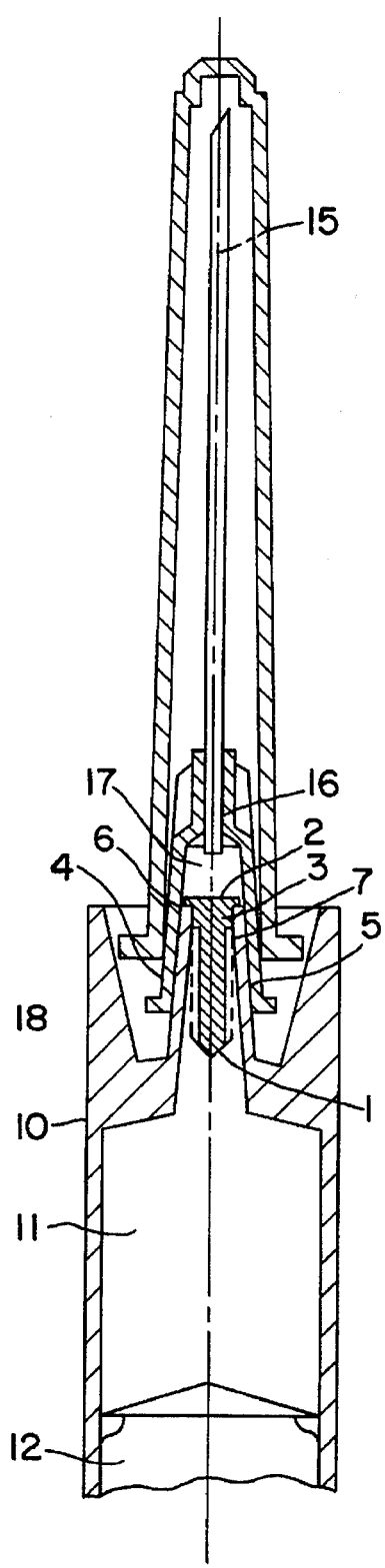
FIG. 6 is a longitudinal section showing all the forming elements located at the place of use and the valve plug of the invention in close position.
Figure 7:
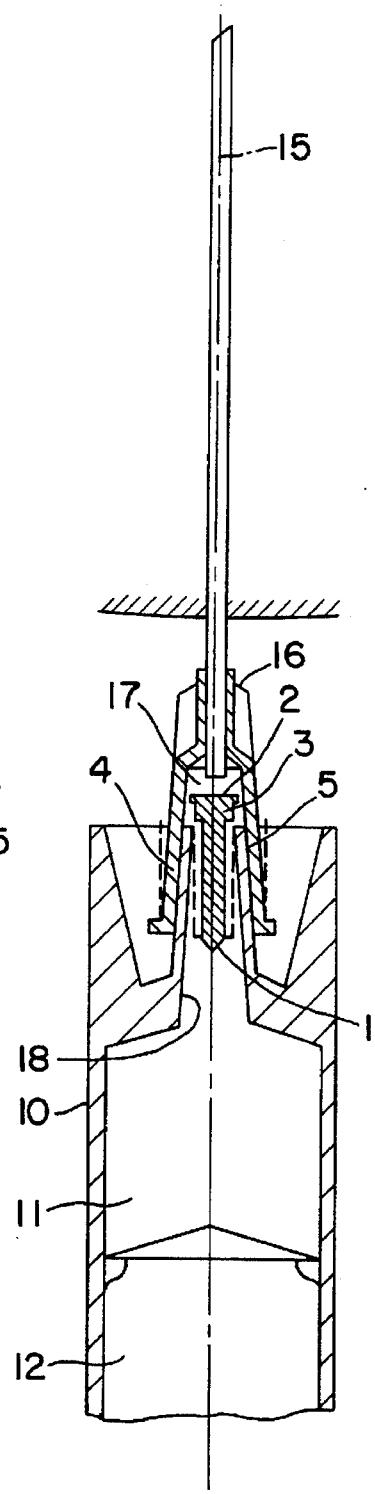
FIG. 7 is another longitudinal section showing the valve plug of the invention in the open position.

FIGS. 5, 6 and 7 show the location of the valve plug and the different positions adopted thereby during its operation.

In fact, numeral 10 designates the body of a pre-filled syringe as those defined above, with its variable volume chamber 11, plunger 12 and plugging cone 18. The plug of the invention is inside the plugging cone 18, with its upper head 2 bearing on the mouth thereof.

The cylindrical portion 3 of the valve plug, snug fits on the wall of the plugging cone providing a tight closure to the interior of chamber 11.

FIG. 6 shows that needle 15, along with its coupling means 16 leaves an internal gap 17 at the portion in which it faces the mouth of the plugging cone 18. This space is used for the automatic operation of the valve plug of the invention.

As shown in FIG. 7, liquid contained in chamber 11, due to the pressure exerted by plunger 12, transmits said pressure at shoulders 6 and 7 of the plug, thus achieving displacement thereof until faceted faces 4 and 5 are in front of the plugging cone mouth, in which case the liquid, free from obstacles, enters into said space 17 and then to the inner conduit supplying the needle 15. Faceted faces 8 and 9 defined at the mentioned head of the valve plug of the invention allow flowing of liquid towards the injection needle.

The construction of conical end 1 of said plug assures that opening hydraulic pressure be effected directly at the portion making the closure, thus being uniform and producing the required displacement.

Figure 8:
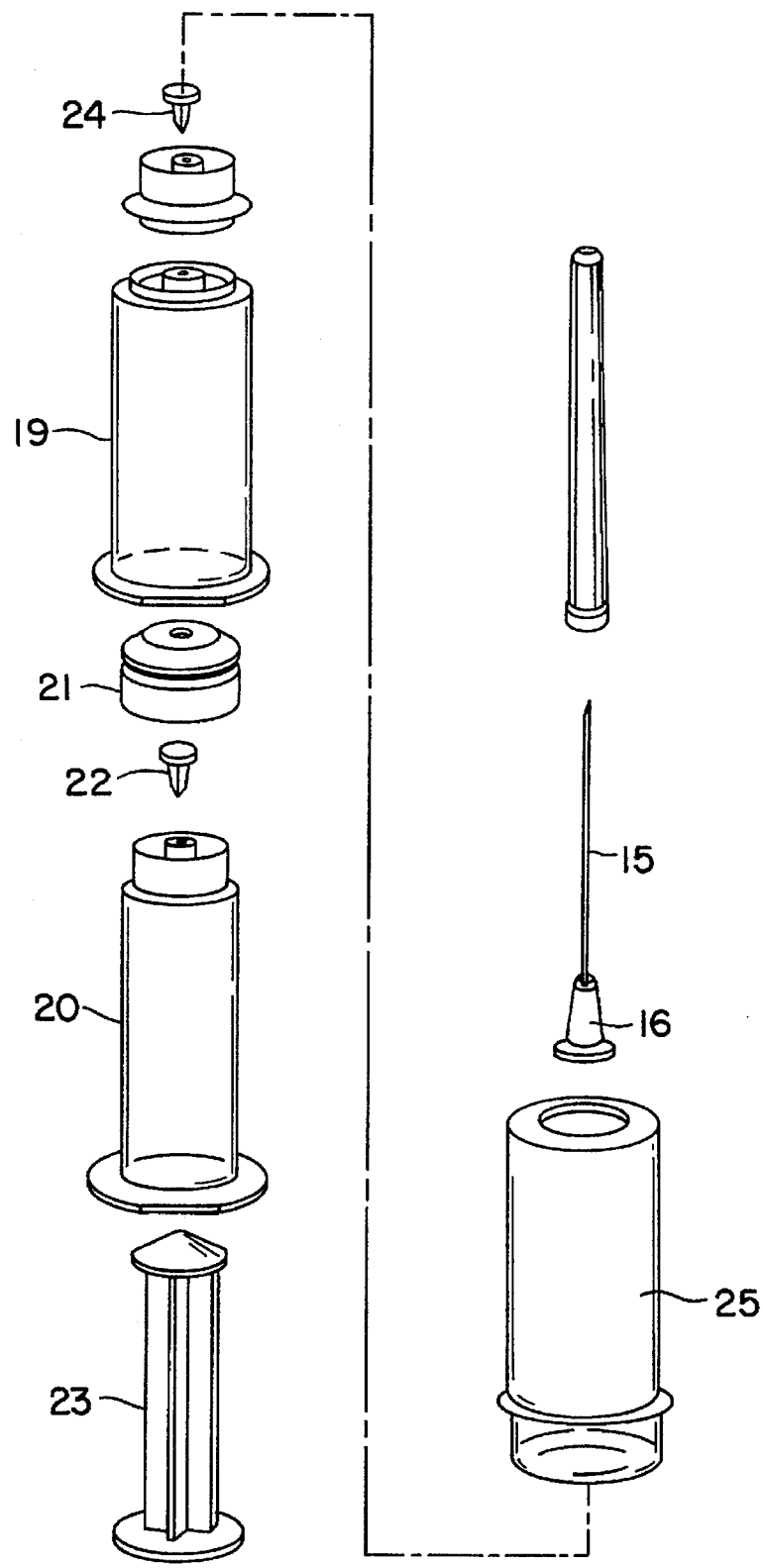
FIG. 8 is an exploded perspective representing a double chamber disposable syringe, according an alternative embodiment of the invention.

FIG. 8 shows another use of the same valve plug, in this case employed in pre-filled double chamber syringes, an upper chamber 19 wherein the solid medium is contained and a lower coaxial chamber 20 wherein the liquid medium is contained.

An elastomeric plug 21 maintains both chambers 19 and 20 separated one from the other, said plug being fixed at the upper end of said lower chamber 20. In this case, the plug of the invention, 22, is placed into the inner conduit communicating both chambers. Upon displacement of plunger 23, the liquid pushes the plug, displacing it into the upper chamber 19 thus allowing mixing of medicine. Plug 22 prevents return of the compound to the lower chamber.

Further, the body of chamber 20 should only be displaced into the body of chamber 19 for injecting; said elastomeric plug 21 acting as plunger head and the already mixed medicine will displace the second valve plug 24 housed with its upper base facing the interior of the plugging cone, as explained in connection with the former embodiment.

Further, these double chamber syringes include a cylindrical body 25 for protecting needles, which is not part of the invention.

We claim:

1. In a syringe for dispensing a fluid from a housing to a needle, a safety valve plug for selectively isolating the fluid in the housing from the needle, said safety valve plug comprising: a disc-shaped head portion having opposed planar surfaces joined together by a sidewall surface; and a substantially cylindrical body extending from one planar surface of said head portion about a longitudinal axis substantially perpendicular to the one planar surface, the cylindrical body having a cylindrical portion extending from the one planar surface, a faceted portion extending from the cylindrical portion and a conical portion extending from the faceted portion.

2. A safety valve plug according to claim 1 wherein the faceted portion has a length along the longitudinal axis greater than the cylindrical portion and the conical portion.

3. A safety valve plug according to claim 1 wherein the faceted portion has two opposed planar surfaces which define with the cylindrical portion a pair of recesses.

4. A safety valve plug according to claim 3 wherein the faceted planar faces defining the recesses are equal and diametrically opposed.

5. A safety valve plug according to claim 1 wherein the disc-shaped head has two opposed planar faceted side faces.

6. A safety valve plug according to claim 1 wherein the disc-shaped head has two equal, diametrically opposed planar faceted side faces.

* * * * *